US00PP25856P3

(12) United States Plant Patent
Yamazaki

(10) Patent No.: US PP25,856 P3
(45) Date of Patent: Sep. 1, 2015

(54) MAITAKE MUSHROOM NAMED 'GRIFON-7'

(50) Latin Name: *Grifola frondosa*
Varietal Denomination: Grifon-7

(71) Applicant: HOKUTO CORPORATION, Nagano (JP)

(72) Inventor: Maki Yamazaki, Nagano (JP)

(73) Assignee: HOKUTO CORPORATION, Nagano (JP)

( * ) Notice: Subject to any disclaimer, the term of this patent is extended or adjusted under 35 U.S.C. 154(b) by 89 days.

(21) Appl. No.: 13/815,955

(22) Filed: Mar. 18, 2013

(65) Prior Publication Data

US 2014/0115743 P1 Apr. 24, 2014

(30) Foreign Application Priority Data

Oct. 18, 2012 (JP) ..... 27470

(51) Int. Cl.
*A01H 15/00* (2006.01)

(52) U.S. Cl.
USPC ..... Plt./394
CPC ..... *A01H 15/00* (2013.01)

(58) Field of Classification Search
USPC ..... Plt./394
See application file for complete search history.

(56) References Cited

U.S. PATENT DOCUMENTS

PP17,984 P3 9/2007 Naganuma et al.

*Primary Examiner* — Anne Grunberg
(74) *Attorney, Agent, or Firm* — Konomi Takeshita

(57) ABSTRACT

The present variety of mushroom plant named 'Grifon-7' was cultivated by the collecting and repeated breeding of Maitake mushrooms having dominant traits, which has good qualitative characteristics and appearance, thick color at the cap surface, white color at the back side of the cap, and excellent cultivability and high yields. This edible mushroom is exquisite in stability, reproducibility and uniformity when being produced.

6 Drawing Sheets

BACKGROUND OF THE INVENTION

This invention relates to a new and distinct variety of mushroom plant of Maitake mushroom, *Grifola frondosa* (Fr.) S. F. Gray. This new variety named 'Grifon-7' cultivated by repeated breeding of Maitake mushrooms having dominant traits, which has thick color of cap surface, white color of back side of cap, excellent cultivability and high yield and ensure presentable stability, reproducibility and uniformity.

Maitake has been artificially cultured and eaten in Japan since long time. The extract of Maitake obtained by hot water extraction contains ingredients that are effective in treatment of cancer because of which there is a great demand of it as a supplement. The demand of fresh Maitake is also increasing. In order to promote the sales of fresh Maitake, it is required that the variety can be cultured easily and the productivity improves. Good external appearance of mushroom, taste, storage characteristics are also important factors to make it appealing to consumers. Although Maitake has been cultured by isolating the strain from the wild variety, however, it has been unsuccessful to artificially control the culture environment that suits the culture of Maitake, because of which it could not be produced in a large scale. Consequently, a new variety called 'Hokuto NT-100', which is easy to culture and has improved quality, taste and storability, was developed as a result of repeated improvements through cross-breeding to improve the stability of culture and quality of mushrooms. This variety has been patented in US (U.S. Plant Pat. No. 17,984 P3). However, the under-face of the cap of the Hokuto NT-100 stained easily which made it look less fresh. Thus, the quality of its appearance was identified as a weakness. To overcome this weakness of Hokuto NT-100, cross-breeding was repeatedly conducted as a result of which a new variety named 'Grifon120' that has a white under-face of cap was developed and having U.S. Plant Pat. No. 21,575. However, it was pointed out that Grifon120 has thin color at the top surface of its cap, because of which it looked less fresh. Consequently, new varieties were developed, from which a new variety was selected and named as 'Grifon-7' after confirming its stability, reproducibility and uniformity.

SUMMARY OF THE INVENTION

The present invention is a new and distinct variety of mushroom characterized particularly by its good qualitative character and appearance, thick color of cap surface, white color of back side of cap, excellent cultivability and high yield, which can be cultivated by collecting and repeated breeding of fungal strains having dominant traits and is exquisite in stability, reproducibility and uniformity when being produced. This novel and distinct variety of mushroom is identified as 'Grifon-7'.

DETAILED DESCRIPTION OF THE INVENTION

The history of the Grifon-7 mushroom in terms of improvement period and the like are set forth in the following chronological list of each stage of variety improvement:

January 1993: Cultivation of Hokuto MY-95.

September 2002: Collected wild Maitake, isolated hyphae and developed strain No. MH182099 in Yamagata of Japan.

February 2004: Hokuto MY-95 and MH182099 were crossed, and the strain having white underface of cap was picked and developed as MH182188.

June 2006: Hokuto NT-100 and Hokuto-carrying strains were crossed, and the strain having thick meat was picked and developed as MH182238.

October 2007: Collected wild Maitake, isolated hyphae and developed strain no. MH182215 in Iwate Prefecture of Japan December 2007: Obtained MH182239 by crossing MH182188 and MH182238.

February 2011: Obtained MH182242 by crossing Hokuto MY-95 and MH182215.

December 2011: Obtained an excellent strain named G110537 by crossing MH182239 and MH182242.

June 2012: Culture test of G110537 was repeatedly conducted and the distinguishability, stability, reproducibility and uniformity were confirmed, upon which the strain was named "Grifon-7" and cultivation was completed.

Figure 7:
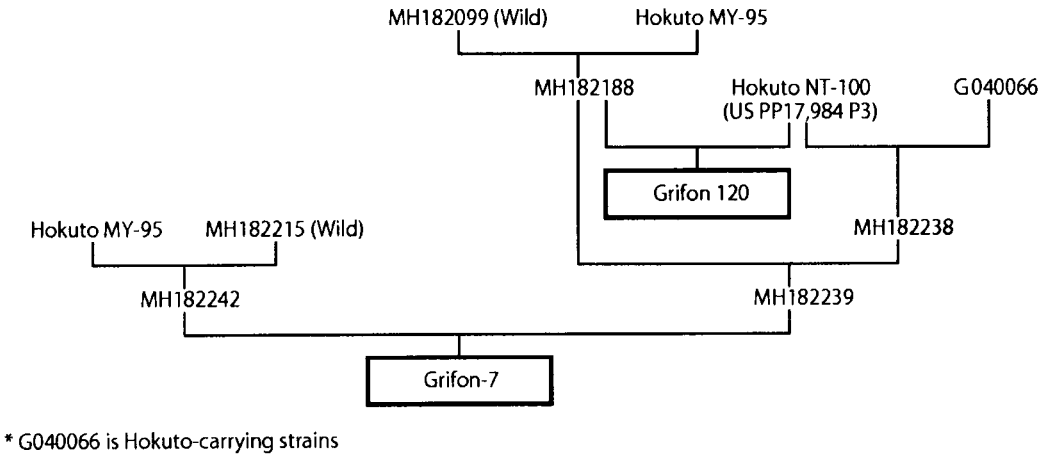
FIG. 7 shows a phylogenetic tree illustrating the antecedents of Grifon 120 and Grifon-7.

October 2012: Applied for registration of new variety to Ministry of Agriculture, Forestry and Fisheries of Japan. On the other hand, Grifon 120 is obtained by crossing MH182188 and Hokuto NT-100, and therefore, Grifon-7 was not developed from Grifon 120. The above crossing is summarized in the phylogenetic tree illustrated in FIG. 7.

The Grifon-7 mushroom has the following characteristics: thick color of cap surface (199A (Grey-Brown Group)), white color of back side of cap (NN155B (White Group)), excellent cultivability and high yield.

(1) Comparison by Dual Culture with Existing Variety

Dislike-touch reaction between Grifon-7 and similar varieties was studied by dual culture.

Study Method:

Grifon-7 and another strain were co-inoculated with an interval of 3 cm by using potato dextrose agar culture medium. Then, the presence/absence of dislike-touch reaction was determined by culturing for 21 days at 25° C.

Strain Used:

| | |
|---|---|
| Grifon-7 (G110537) | Present variety |
| Grifon120 | Varieties similar to the present variety |
| Hokuto NT-100 | Varieties similar to the present variety |
| Hokuto MY-95 | Varieties similar to the present variety |

Results:

Grifon-7 showed dislike-touch reaction with all other co-cultured varieties (See Table 1 and FIGS. 1 to 4). These results show that the present strain is a new variety.

TABLE 1

| Results of dual culture | | | | |
|---|---|---|---|---|
| | Similar variety | | | |
| | Grifon-7 | Grifon120 | NT-100 | MY-95 |
| Grifon-7 | – | + | + | + |

+ is present and – is absent.

(2) Cultural Characteristics of Grifon-7

When Grifon-7 was cultured in potato dextrose agar culture medium, hyphae color was white, hyphal density was medium, shape of colony periphery was heterogeneous, thickness was medium, and surface was island.

After inoculating a small piece of Grifon-7 measuring 5 mm diameter in potato dextrose agar culture medium, it was cultured 5-30° C. with 5° C. interval. When the mean mycelial growth rate per day was calculated from the mycelial growth of 10-day culture, it was found that the mean mycelial growth rate was the highest at 26° C.

The mycelial growth rate at 10° C. was fast with 1.31 mm/day, while the growth of similar variety Grifon120 was slow at 0.56 mm/day. Also, mycelial growth rate at 15° C. was fast at 2.11 mm/day, while the growth of Grifon120 was medium at 1.68 mm/day. The mycelial growth rate at 30° C. was medium at 2.57 mm/day, while the growth of Grifon120 was slow at 0.89 mm/day. From the above results, it can be understood that the strain is clearly different from Grifon120.

(3) Morphological Characteristics Based on an Example of Grifon-7 Cultivation

Cultivation Method (Bag) A polypropylene culture bag (Square-shaped, capacity: 8500-9000 cc, mouth diameter: 200×120 mm, height: approx. 440 mm, air filter present) was used. Altogether 48 bags were used, and cultivation was repeated three times in each in 16 bags.

(Substrate) Sawdust of broadleaf tree, which is mainly beechwood, and corn bran were mixed in the dry-weight ratio of 75:25, and the mixture was adjusted to 60%-62% water content. The substrate was filled at the rate of 2.5 kg per bag, and was sterilized at high pressure.

(Spawn) Sawdust spawn was used. About 25 cc of the spawn was inoculated per bag.

(Culture) Culture was conducted under 20° C.-22° C. temperature, 70-75% humidity and 200-500 lux luminosity, and the cultivar that have primordia formation are shifted to the growing room.

(Growth) The primordia forming bag-culture was shifted to a 17° C.-18° C. temperature, 90-95% humidity and 500-1500 lux luminosity environment to promote the growth of primordia. After the primordia grows up to the extent of touching the filter part, the filter part is taken out and growth of fruit body is promoted. The mushroom is harvested when the pore on the back side of cap about 2-3 mm from the edge.

Cultivation Results

The characteristics of Grifon-7 cultivated under the conditions mentioned above, and the specific difference in characteristics with the most similar variety Grifon120 are explained in Table 2 below.

Figure 1B:
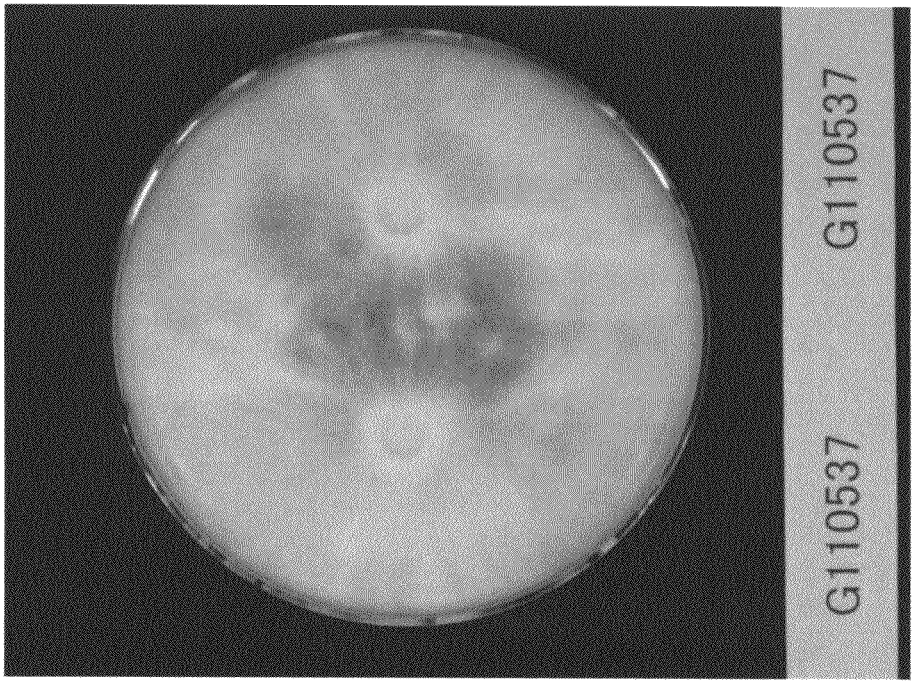
FIGS. 1A and 1B respectively show front and back images of dual-culture of Grifon-7 (G110537) colony.
Figure 1A:
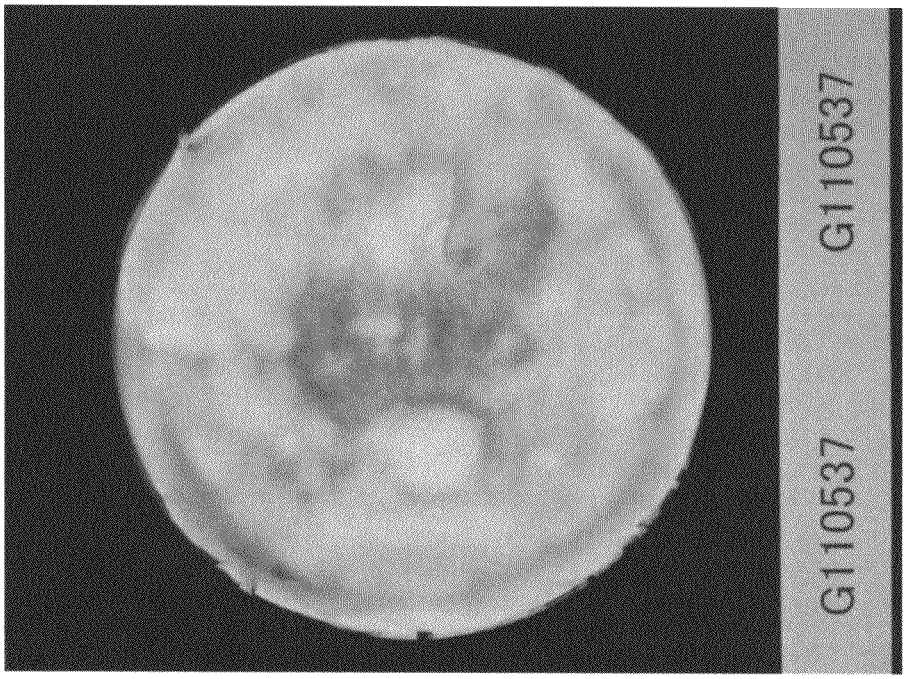
Figure 2B:
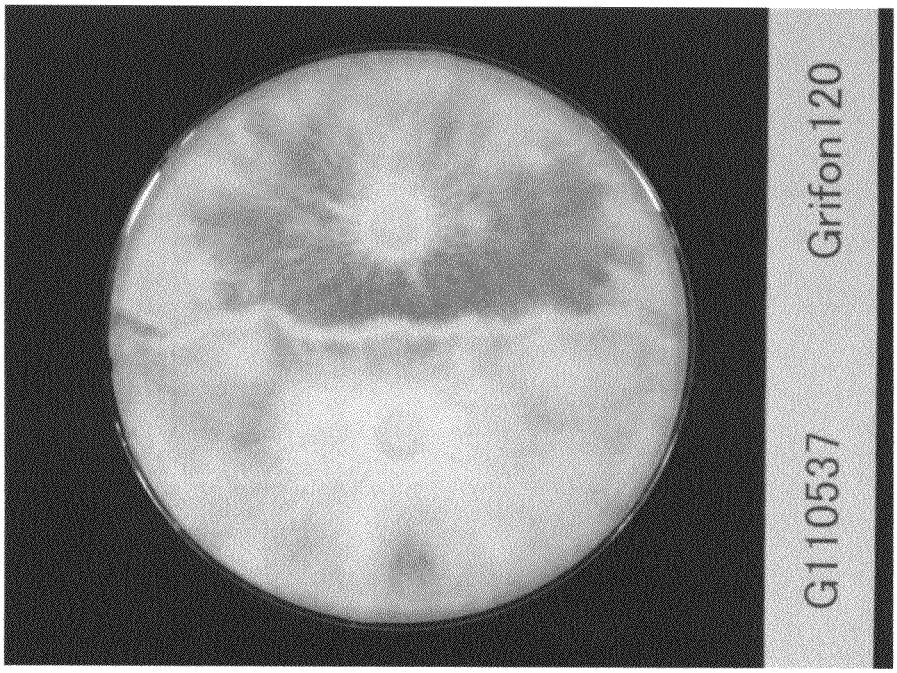
FIGS. 2A and 2B respectively show front and back images of dual-culture of Grifon-7 (G110537) and Grifon120.
Figure 2A:
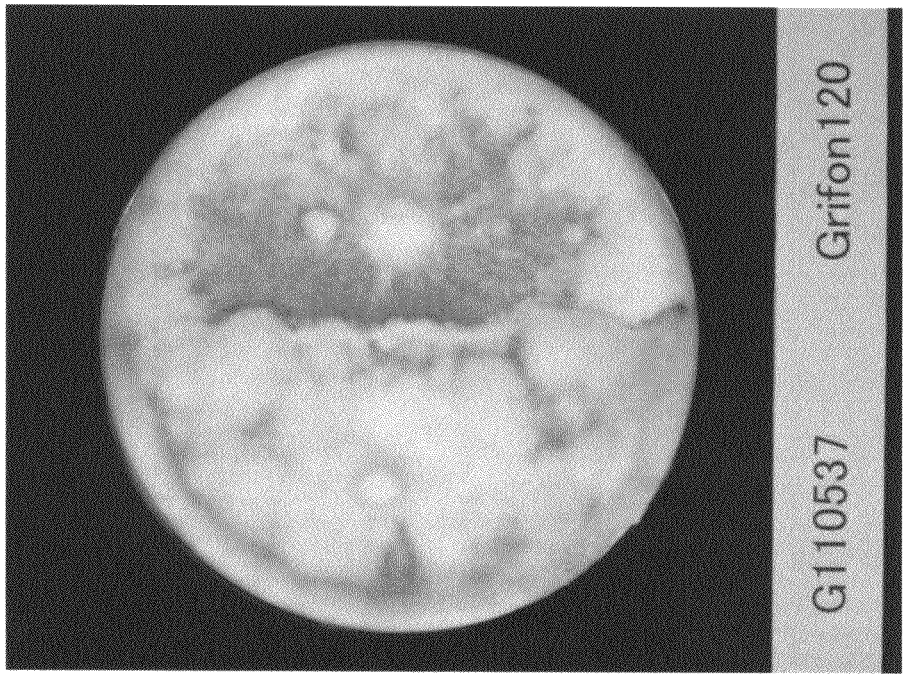
Figure 3B:
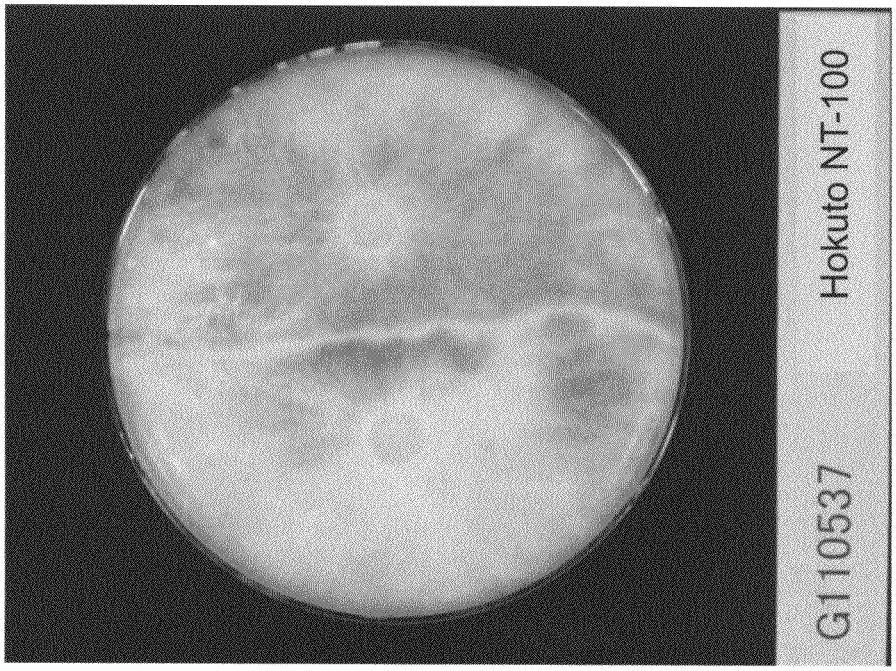
FIGS. 3A and 3B respectively show front and back images of dual-culture of Grifon-7 (G110537) and Hokuto NT-100.
Figure 3A:
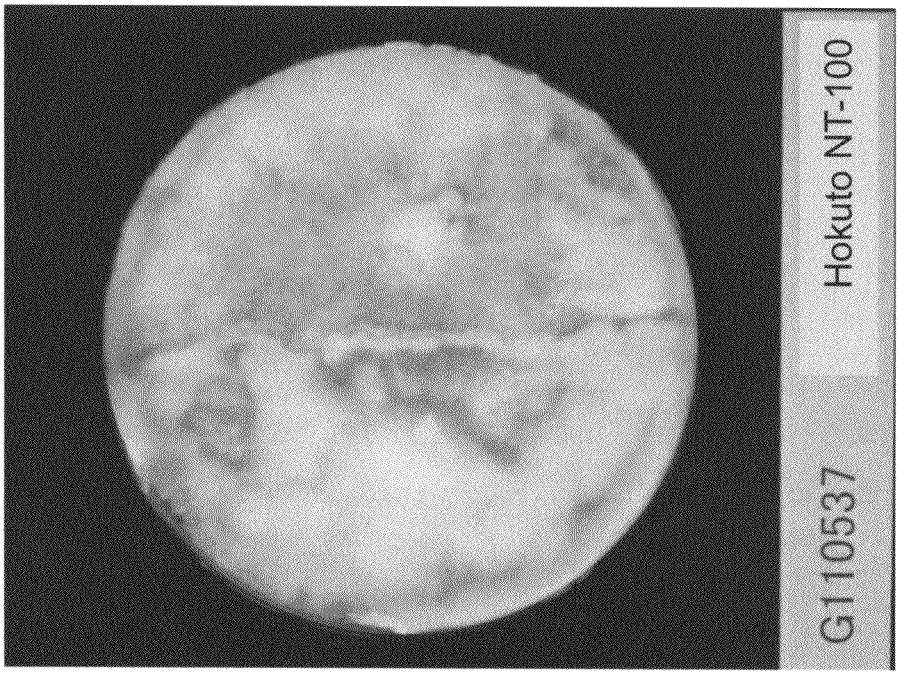
Figure 4B:
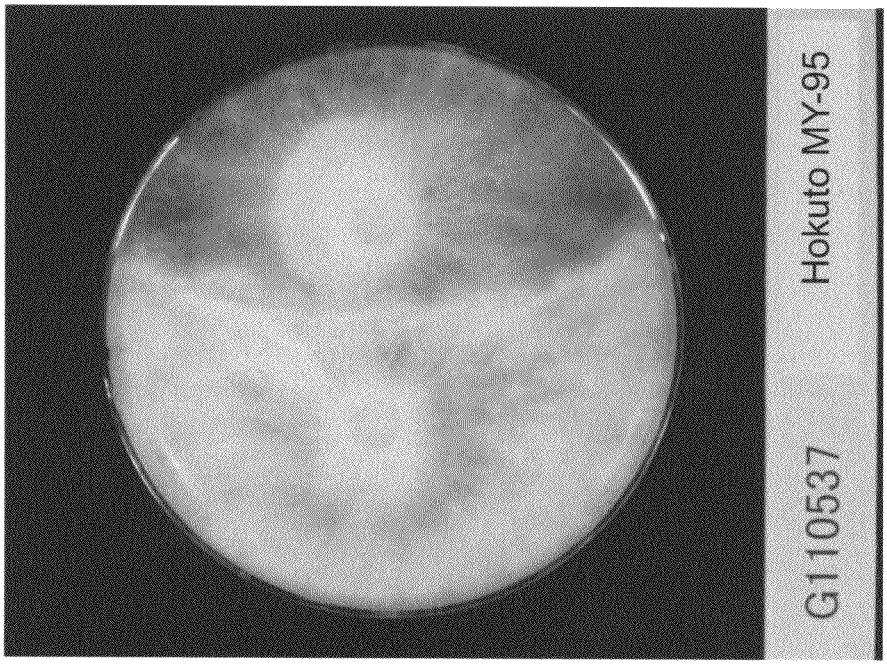
FIGS. 4A and 4B respectively show front and back images of dual-culture of Grifon-7 (G110537) and Hokuto MY-95.
Figure 4A:
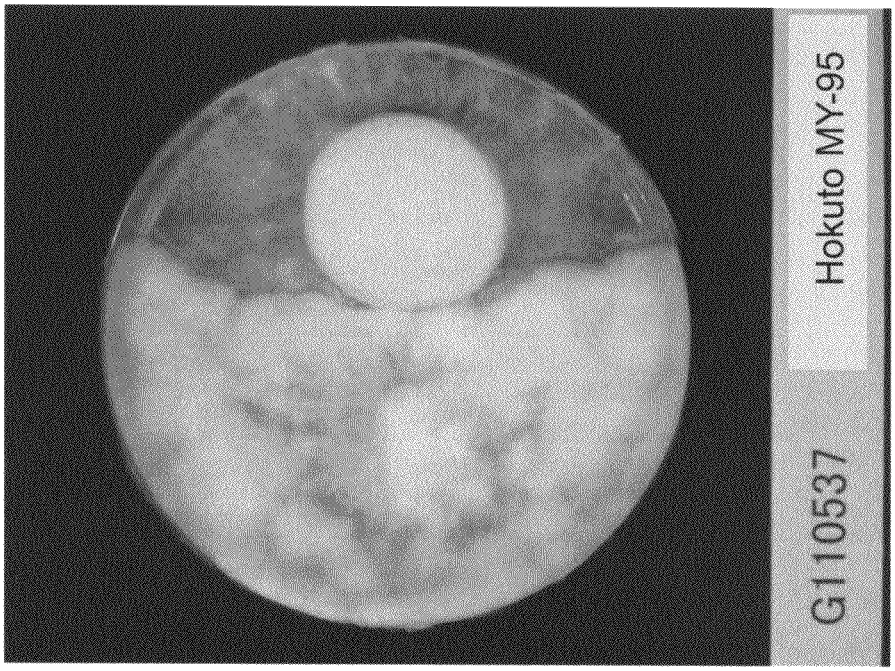
Figure 5:
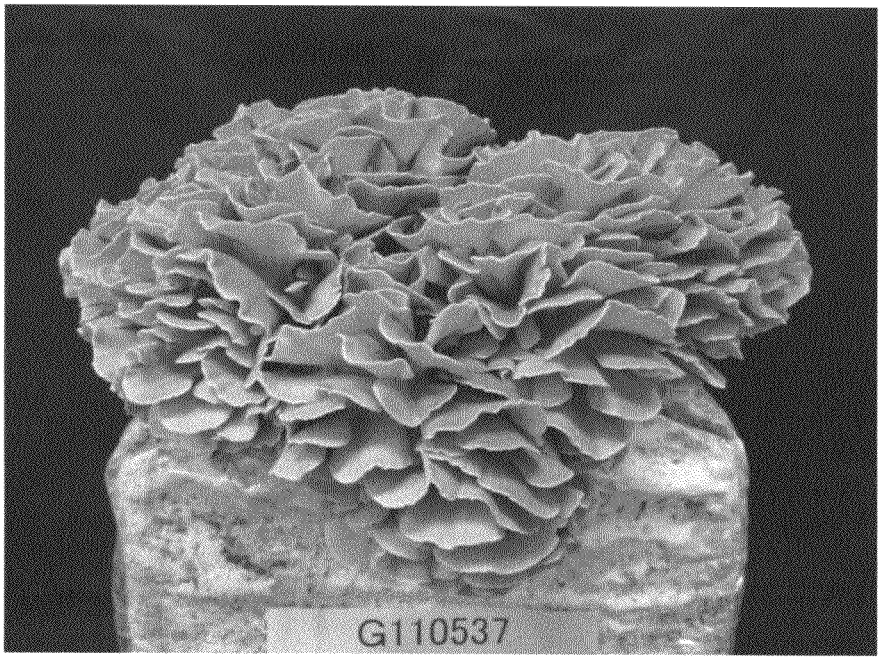
FIG. 5 shows image of fruit body of Grifon-7 (G110537).
Figure 6:
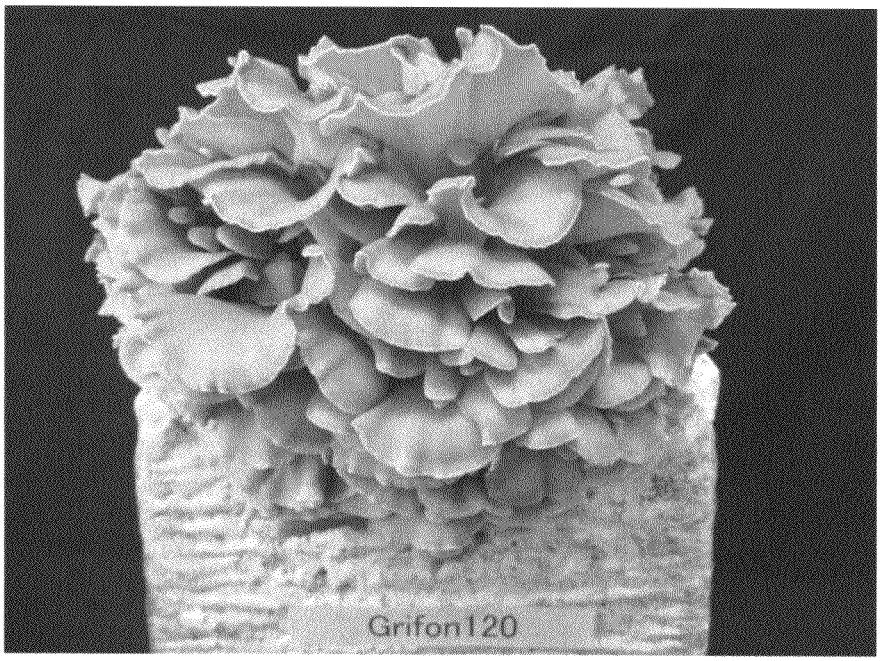
FIG. 6 shows image of fruit body of Grifon120.

Also, the images of the respective fruit bodies have also been attached. (See FIGS. 5 and 6).

TABLE 2

| | present variety Grifon-7 | similar variety Grifon120 |
|---|---|---|
| Mycelial growth rate | | |
| 10° C./day | 1.31 mm | 0.56 mm |
| 15° C./day | 2.11 mm | 1.68 mm |
| 20° C./day | 2.74 mm | 2.36 mm |
| 25° C./day | 3.29 mm | 3.04 mm |
| 30° C./day | 2.57 mm | 0.89 mm |
| Diameter of a cluster on a bag | 20.17 ± 0.91 cm | 20.44 ± 1.07 cm |
| Cap | | |
| Diameter | 30.14 ± 4.98 mm | 36.27 ± 5.68 mm |
| Thickness | 1.98 ± 0.28 mm | 2.03 ± 0.27 mm |
| Shape | Fan | Fan |
| Observe a shape of vertical section | Level | 45 lower parts |
| Color of surface | 199A (Grey-Brown Group) | 199C (Grey-Brown Group) |
| Hardness | Medium | Medium |
| Shape of zonate spots of the surface | Peripheral part | Peripheral part |
| Development part of pore | Whole of cap | Whole of cap |

TABLE 2-continued

| | present variety Grifon-7 | similar variety Grifon120 |
|---|---|---|
| Tinting of mycelial mat of the surface of bag-culture | Absent | Absent |
| Period from inoculation to primordia formation | 36.8 ± 1.38 days | 35.4 ± 1.20 days |
| Period from inoculation to harvest | 45.4 ± 1.33 days | 44.9 ± 0.87 days |
| Optimum temperature for fruit body development | 18-20° C. | 18-20° C. |
| Fresh weight of fruit body per 2.5 kg sawdust-based bag-culture | 897.3 ± 48.34 g | 855.9 ± 34.85 g |
| Dual culture | | |
| Dislike-touch reaction of colony | Present | |

* The employed color chart is an R.H.S Colour Chart prescribed by the Royal Horticultural Society, England.

What is claimed is:

1. A new, distinct variety of Maitake mushroom as substantially illustrated and described in the specification.

* * * * *

* G040066 is Hokuto-carrying strains